United States Patent [19]

Harris et al.

[11] 3,941,782

[45] Mar. 2, 1976

[54] HETEROCYCLIC ESTERS OF BENZOPYRANS

[75] Inventors: Louis Selig Harris, Chapel Hill, N.C.; Harry George Pars, Lexington, Mass.; Raj Kumar Razdan, Belmont, Mass.; John Clark Sheehan, Lexington, Mass.

[73] Assignee: Sharps Associates, Cambridge, Mass.

[22] Filed: May 21, 1973

[21] Appl. No.: 361,897

Related U.S. Application Data

[63] Continuation-in-part of Ser. No. 248,308, April 27, 1972, abandoned, which is a continuation-in-part of Ser. No. 143,688, May 12, 1971, abandoned.

[52] U.S. Cl.. 260/243 B; 260/247.2 B; 260/293.58; 260/326.34; 260/345.3; 424/246; 424/248; 424/267; 424/274; 424/283
[51] Int. Cl.² ..................... C07D 311/78
[58] Field of Search .... 260/247.2 B, 293.58, 243 B, 260/326.34, 345.3

[56] References Cited
UNITED STATES PATENTS 3,654,312 4/1972 Pars et al. ............. 260/293.58
3,676,462 7/1972 Pars et al. ............. 260/293.58

*Primary Examiner*—Richard J. Gallagher
*Attorney, Agent, or Firm*—Merriam, Marshall, Shapiro & Klose

[57] ABSTRACT

This invention relates to novel esters of benzopyrans represented by the formulae

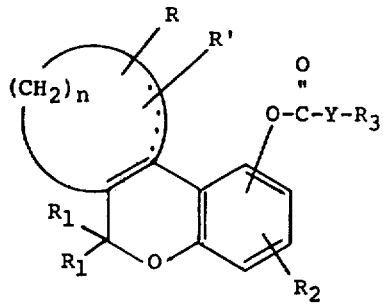

and

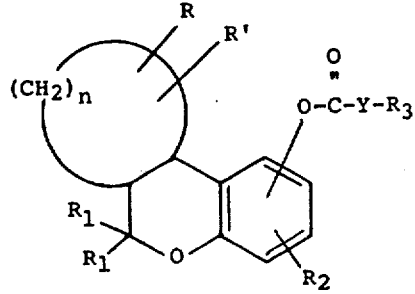

wherein R and R' are hydrogen or $C_1-C_6$ alkyl and when alkyl are on the same or different carbons; $R_1$ is $C_1-C_6$ alkyl; $R_2$ is $C_1-C_{20}$ alkyl, lowercycloalkyloweralkyl or lowercycloalkyl; $n$ is an integer from 3 to 7, and particularly 3 to 5; Y is a straight or branched chain $C_1-C_8$ alkylene; and $R_3$ is

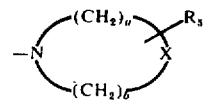

wherein $a$ is an integer from 1 to 4, $b$ is an integer from 1 to 4, X is O, S, $CH_2$ or $NR_4$ and $R_4$ is hydrogen $C_1-C_6$ alkyl, and $R_5$ is hydrogen or $C_1-C_6$ alkyl; and the acid addition salts thereof. The compounds exhibit analgesic and central nervous system activity.

20 Claims, No Drawings

HETEROCYCLIC ESTERS OF BENZOPYRANS

CROSS-REFERENCE TO RELATED APPLICATIONS

This application is a continuation-in-part of copending U.S. application Ser. No. 248,308 filed Apr. 27, 1972 which is a continuation-in-part of copending application Ser. No. 143,688 filed May 12, 1971, both now abandoned. The complete content and disclosure of these applications is incorporated herein by reference.

DETAILED DESCRIPTION OF THE INVENTION

This invention relates to novel esters of benzopyrans, to compositions containing such compounds and to methods for preparing and using the novel compounds. The compounds of this invention are represented by the formulae:

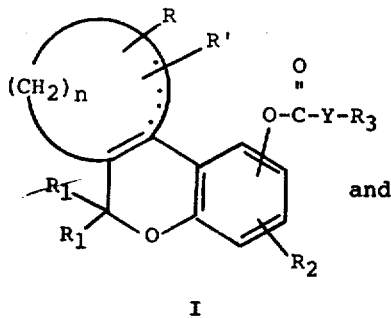

and

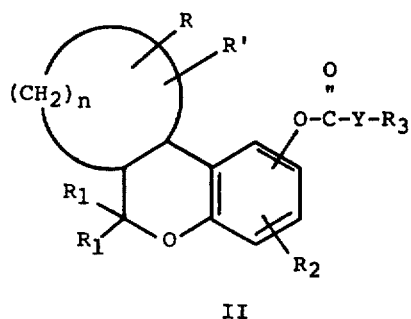

wherein R and R' are hydrogen or $C_1-C_6$ alkyl; $R_1$ is $C_1-C_6$ alkyl; $R_2$ is $C_1-C_{20}$ alkyl, lowercycloalkyl-loweralkyl or lowercycloalkyl; $n$ is an integer from 3 to 7, particularly 3 to 5; Y is a straight or branched chain $C_1-C_8$ alkylene; and $R_3$ is

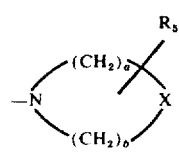

wherein $a$ is an integer from 1 to 4, $b$ is an integer from 1 to 4, X is O, S, $CH_2$ or $NR_4$, and $R_4$ is hydrogen or $C_1-C_6$ alkyl and $R_5$ is hydrogen or $C_1-C_6$ alkyl; and the acid addition salts thereof.

The series of dots in Formula I indicate that the double bond in the c ring can be located in any one of several positions in that ring.

In one preferred embodiment of this invention, the sum of $a + b$ is at least 3 and Y is a straight or branched $C_2-C_6$ alkylene. It is further presently preferred that when X is O, S, or $NR_4$, that the sum of $a + b$ is at least 4 and preferably $a$ and $b$ each are 2.

The term "$C_1-C_6$ alkyl" as used herein, refers to both straight and branched chain alkyl radicals including methyl, ethyl, n-propyl, iso-propyl, n-butyl, sec-butyl, tert-butyl, n-pentyl, iso-pentyl, neo-pentyl, n-hexyl and the like.

The term "$C_1-C_{20}$ alkyl" includes straight or branched chain alkyl radicals of from 1–20 carbon atoms including for example, methyl, n-amyl, n-hexyl, 2-heptyl, n-heptyl, 3-methyl-2-octyl, n-octyl, γ-nonyl, 2-tetradecyl, 2-eicosanyl and the like.

"Lowercycloalkyl" refers to $C_3$ to $C_8$ cycloalkyl groups.

"Halo" includes chloro, fluoro, bromo and iodo.

The term "acid addition salts" refers to non-toxic salts prepared for example, by reacting the basic esters with an organic or inorganic acid. Representative salts include the hydrochloride, hydrobromide, sulfate, bisulfate, acetate, valerate, oleate, laurate, borate, benzoate, lactate, phosphate, tosylate, citrate, meleate, succinate, tartrate and the like. Such salts are well known in the art and are considered to be "pharmaceutically acceptable".

When, for example, $n$ is 3, the preferred compounds are represented by formulae III, IV and V.

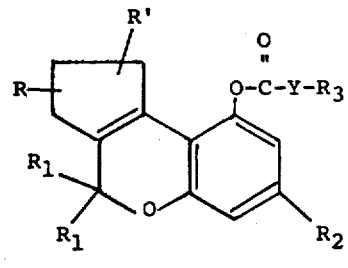

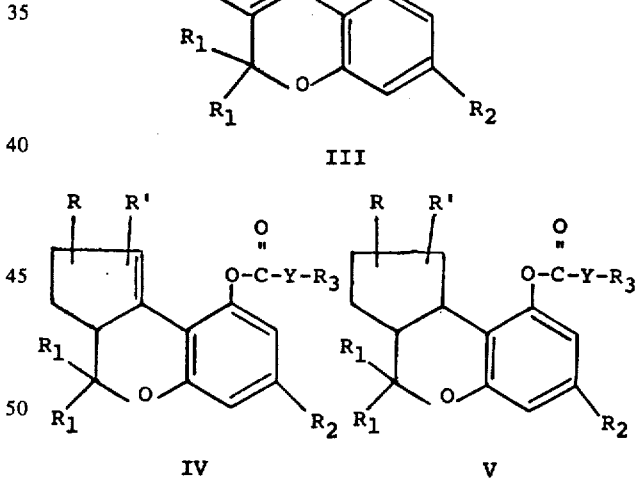

When $n$ is 4, the preferred compounds are represented by formulae VI, VIa, VII and VIII.

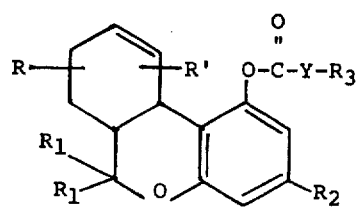

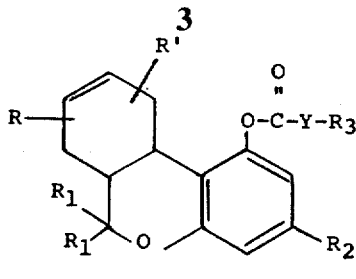

VIa

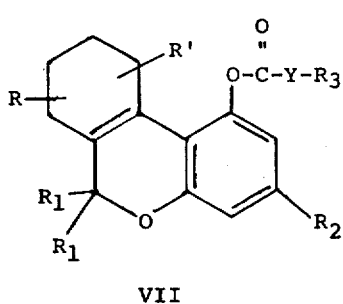

VII

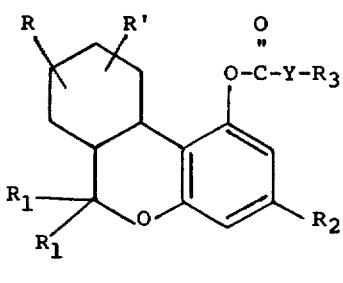

VIII

The compounds of Formulae III to VIII in which R is hydrogen or methyl and R' is hydrogen or methyl are specially preferred compounds.

The compounds of this invention exhibit analgesic and central nervous system activity, and are useful as analgesic agents, mild tranquilizers and sedative-hypnotics.

Analgesia is obtained at dosages of from 20 to 40 mg./kg. of body weight orally and from 10 to 20 mg./kg. of body weight intraperitoneally (i.p.). The analgesic activity was first established using the rat tail flick method of Harris, et al., J.P.E.T. 169, 17 (1969) and the hot plate analgesia test, and confirmed in the mouse writhing test.

The compounds exhibit mild tranquilizing activity in mice at dosages of from 5 to 40 mg./kg. intraperitoneally and in dogs at dosages of from 1 to 5 mg./kg. orally. If tranquilization is desired during the day, lower dosages are administered. If the higher dosages are administered, the compounds are useful as sedative-hypnotics and can be employed to induce sleep.

Generally speaking, the esters of this invention are prepared by reacting equimolar quantities of the corresponding benzopyran, a carbodiimide, such as for example dicyclohexylcarbodiimide, and the appropriate acid or its acid addition salt in a suitable solvent such as methylene chloride, chloroform and the like, for from 2 to 72 hours. The reaction is followed with thin layer chromatography, preferably in 10% methanol/chloroform. The mixture is then cooled in ice and filtered to remove the by-product of dicyclohexylurea. The solvent is evaporated by, for example, employing a vacuum rotary evaporator and the residue is dissolved in, for example, benzene. The solution is filtered again to remove any suspended impurities and the product is either crystallized from suitable solvents such as benzene/ether or the residue can be chromatographed and the product isolated from the appropriate chromatographic fractions. If the basic esters are obtained, the acid addition salts can readily be prepared by reacting the ester with an appropriate organic or inorganic acid. The reaction is represented by the following reaction scheme:

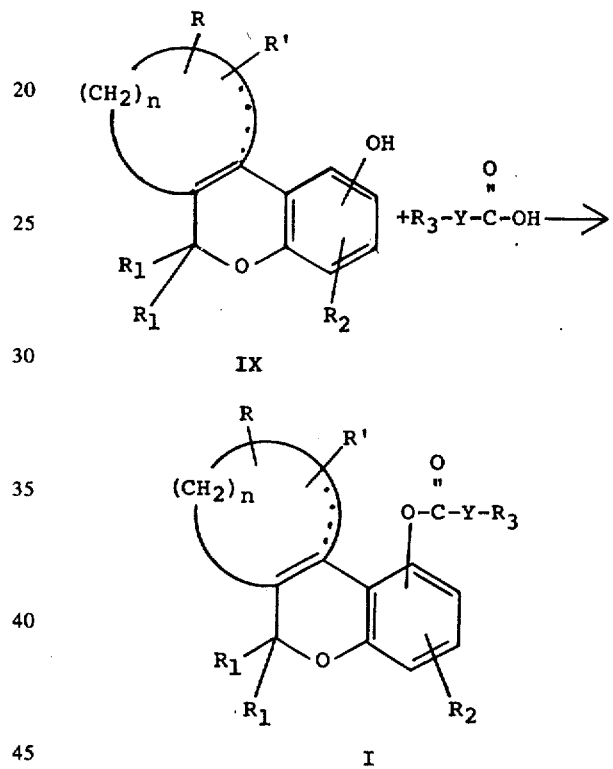

wherein R, R', $R_1$, $R_2$, $R_3$, Y and $n$ have the previously designated significance.

Benzopyrans which can be used as starting materials are disclosed by Adams et al. in J. Am. Chem. Soc., 62, 2245 and 2407 (1940); Adams et al. J. Am. Chem. Soc. 67, 1534 (1945), Mechoulam et al. J. Am. Chem. Soc. 89, 4552 (1967); Bergel et al. J. Chem. Soc. 286 (1943); Avison et al. J. chem. Soc. 952 (1949); Ghosh et al. J. Chem. Soc. 1118 (1940); Aaron et al. J. of Organic Chem. 33, 684 (1968); Taylor et al. Tetrahedron 23, 77 (1967) and United States Pat. Nos. 2,419,936; 3,388,136. Other benzopyran starting materials which may not be specifically disclosed in the prior art can be readily produced according to known procedures by reacting a 5-$R_2$-resorcinol, in which $R_2$ has the previously assigned significance, with a 2-carboloweralkoxy cyclopentanone, cyclohexanone, or other cycloalkanone, many of which are disclosed in Organic Reactions, Volume 15, John Wiley & Sons, Inc., 1967, as see for example pages 51, 52, 61 and 62.

Some of the heterocylic acids which can be used in the process of making the compounds provided by the invention are:
γ-piperidinobutyric acid,
γ-morpholinobutyric acid,
γ-(2-methylpiperidino)-butyric acid,
δ-piperidinovaleric acid,
γ-pyrrolidinobutyric acid,
β-piperidinopropionic acid,
γ-thiomorpholinobutyric acid,
homopiperidinoacetic acid,
β-thiomorpholinopropionic acid and
α-methyl-γ-piperidinobutyric acid.

Some of the benzopyrans which can be used as starting materials are: 4,4-dimethyl-9-hydroxy-7-(3-methyl-2-octyl)-1,2,3,4-tetrahydrocyclopenta[c]]1]benzopyran, 4,4-di-(1-hexyl)-9-hydroxy-7-(3-methyl-2-octyl)-1,2,3,4,12,13-hexahydrocyclopenta[c][1]benzopyran, 4,4-dimethyl-9-hydroxy-7-(3-methyl-2-octyl)-1,2,3,4,12,13-hexahydrocyclopenta[c][1]benzopyran, 4,4-diethyl-9-hydroxy-7-octadecyl-1,2,3,4,12,13-hexahydrocyclopenta[c][1]benzopyran, 1-hydroxy-3-pentyl-6a,7,8,10a-tetrahydro-6,6,9-trimethyl-6H-dibenzo[b,d]pyran also called Δ⁹-tetrahydrocannabinol, 1-hydroxy-3-pentyl-6a,7,10,10a-tetrahydro-6,6,9-trimethyl-6H-dibenzo [b,d]pyran also called Δ⁸-tetrahydrocannabinol, 1-hydroxy-3-(3-methyl-2-octyl)-7,8,9,10-tetrahydro-6H-dibenzo[b,d]-pyran, 1-hydroxy-3-pentyl 6a,7,8,9,10a-hexahydro-6H-dibenzo[b,d]pyran, -methyl-9-hydroxy-7-(3 -methyl-2-octyl)-1,4,4-trimethyl-1,2,3,4,-tetrahydrocyclopenta[c][1]benzopyran, 9-hydroxy-7-(3-methyl-2-octyl)-2,4,4-trimethyl-1,2,3,4,-tetrahydrocyclopenta[c][1]benzopyran, 9-hydroxy-7-(3-methyl-2-octyl)-2,2,4,4-tetramethyl-1,2,3,4,-tetrahydrocyclopenta[c][1]-benzopyran, 1-ethyl-4,4-dimethyl-9-hydroxy-7-(3-methyl-2-octyl)-1,2,3,4,-tetrahydrocyclopenta[c][1]-benzopyran and 1-hydroxy-3-(3-methyl-2-octyl)-7,8,9,10-tetrahydro-6,6,10-trimethyl-6H-dibenzo[b,d]pyran.

Some of the compounds produced according to the invention are: 4,4-diethyl-7-n-pentyl-9-[4-(piperidino)-butyryloxy]-1,2,3,4-tetrahydrocyclopenta[c][1]benzopyran, 4,4-di-(1-hexyl)-7-(3-methyl-2-octyl)-9-[4-(morpholino)-butyryloxy]-1,2,3,4,12,13-hexahydrocyclopenta[c][1]benzopyran, 4,4-dimethyl-7-(3-methyl-2-octyl)-9-[4-(piperidino)-butyryloxy]-1,2,3,4,12,13-hexahydrocyclopenta[c][1]benzopyran, 4,4-diethyl-7-octadecyl-9-[3-pyrrolidino)-propionyloxy]-1,2,3,4,12,13-hexahydrocyclopenta[c][1]benzopyran, 3-pentyl-1-[4-(thiomorpholino)-butyryloxy]-6a,7,8,10a-tetrahydro-6,6,9-trimethyl-6H-dibenzo[b,d]pyran, 3-pentyl-1-[3-(pyrrolidino)-propionyloxy]-6a,7,10,10a-tetrahydro-6,6,9-trimethyl-6H-dibenzo[b,d]pyran, 1-[4-(homopiperidino)-butyryloxy]-7,8,9,10-tetrahydro-6H-dibenzo-[b,d]pyran and 1-[4-(morpholino)-butyryloxy]-3-pentyl-6a, 7,8,9,10,10a hexahydro-6H-dibenzo[b,d]pyran.

The present invention includes within its scope pharmaceutical compositions comprising, as an active ingredient, at least one of the compounds of this invention in association with a pharmaceuticlly acceptable carrier or diluent. The compounds of this invention exhibit both oral and parenteral activity and can be formulated in dosage for oral, parenteral or rectal administration.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate, and sweetening and flavoring agents. Tablets and pills can additionally be prepared with enteric coatings.

Liquid dosage forms for oral administration include pharmaceutically accpetable emulsions, solutions, suspensions, syrups and elixirs containing inert diluents commonly used in the art, such as water. Besides inert diluents, such compositions can also include adjuvants, such as wetting agents, emulsifying and suspending agents and sweetening, flavoring and perfuming agents.

Preparations according to this invention for parenteral administration include sterile aqueous or non-aqueous solutions, suspensions or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal administration are suppositories which may contain in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration and on the duration of the treatment. Generally, dosage levels of between 1 to 40 mg./kg. of body weight daily are administered to patients in need of analgesia or tranquilization.

The following is an illustration of the pharmaceutical compositions which are a feature of this invention:

TABLET COMPOSITION

Tablets weighing 200 mg. and having the following composition are prepared by standard tableting procedures:

| Ingredient | Mg. |
|---|---|
| 4,4-Dimethyl-7-(3-methyl-2-octyl)-9-[4-(piperidino)-butyryloxy]-1,2,3,4-tetrahydrocyclopenta-[c][1]benzopyran hydrochloride | 100 |
| Starch | 90 |
| Colloidal silica | 5 |
| Magnesium stearate | 1 |

It will be understood by those skilled in the art that the above composition can contain any of the compounds of this invention.

The following examples further illustrate the present invention:

EXAMPLE 1

4,4-Dimethyl-9-hydroxy-7-(3-methyl-2-octyl)-1,2,3,4-tetrahydrocyclopenta[c][1]benzopyran a. 4-Oxo-9-hydroxy-7-(3-methyl-2-octyl)-1,2,3,4,-tetrahydrocyclopenta[c][1]benzopyran A mixture of 8.5 g. (0.0545 mole) of ethyl cyclopentanone-2-carboxylate (Aldrich Chemical Co.), 11.6 g. (0.05 mole) of 5-(3-methyl-2-octyl)resorcinol, and 5.6 g. (3.5 ml; 0.0365 mole) of phosphorous oxychloride was heated under reflux in 50 ml. of benzene for 5 hours. The mixture turned deep red. The cooked solution was added to an excess sodium carbonate/ice mixture and the mixture was then extracted with ether. The organic layer was washed with water, dried and evaporated to give a solid which crystallized from an ethyl acetate/petroleum ether mixture as colorless crystals, m.p. 151°–154°C. Recrystallization from methanol containing a few drops of water gave the desired pyrone as colorless crystals, m.p. 154°–156°C. Nuclear magnetic resonance confirmed the assigned structure.

Analysis Calcd. for $C_{21}H_{28}O_3$: C, 76.79; H, 8.58. Found: C, 76.98; H, 8.55.

b. 4,4-Dimethyl-9-hydroxy-7-(3-methyl-2-octyl)-1,2,3,4-tetrahydrocyclopenta[c][1]benzopyran A solution of 3.28 g. (0.01 mole) of the above prepared pyran, m.p. 154°–156°C., in 30 ml. of benzene was added to a refluxing solution of methyl magnesium iodide, prepared from 2.4 g. (0.1 mole) of magnesium turnings and 14.2 g. (0.1 mole) of iodomethane in 30 ml. of ether. The mixture was refluxed for 16 hours and decomposed with an ice and ammonium chloride mixture. The organic layer was separated and the aqueous layer was extracted with benzene. The combined extracts were washed with water and dried. After evaporation of the solvent, the residue was taken up in n-heptane and boiled with a few drops of hydriodic acid for 20 minutes. A violent reaction occurred. The solution was cooled, treated with decolorizing carbon, and evaporated to a gum. The gum was distilled at 0.05 mm through a short path distillation apparatus to give 1.9 g. of the desired product as an amber colored liquid (pot temperature, 230°C.). Ultraviolet and nuclear magnetic resonance analysis confirmed the structure.

Analysis Calcd. for $C_{23}H_{34}O_2$: C, 80.65; H, 10.01. Found: C, 80.59; H, 9.96.

EXAMPLE 2

4,4-Dimethyl-7-(3-methyl-2-octyl)-9-[4-(piperidino)butyryloxy]-1,2,3,4-tetrahydrocyclopenta[c][1]benzopyran hydrochloride

5.0 g. (14.6 mmoles) of 4,4-dimethyl-9-hydroxy-7-(3-methyl-2-octyl)-1,2,3,4-tetrahydrocyclopenta[c][1]benzopyran, 3.14 g. (15.2 mmoles) of dicyclohexylcarbodiimide and 3.15 g. (15.2 mmoles) of γ-piperidinobutyric acid hydrochloride (m.p. 190°–192°), Cruickshank & Sheehan J. Am. Chem. Soc. 83, 2891 (1961), were combined with 250 ml. of methylene chloride and stirred for a total of 40 hours at room temperature. The insoluble by-product of dicyclohexylurea was separated by filtration and the methylene chloride was removed using a rotary evaporator. The brown residue was treated with approximately 75 ml. of benzene, and filtered to remove a small amount of insoluble material. The benzene was evaporated and the brown, viscous residue was triturated with about 200 ml. of ether to give 4.3 g. of crude product as a light brown solid, m.p. 174°–176°C. Recrystallization from benzene gave a total of 3.5 g. (45%) of product as colorless crystals, m.p. 174°–176°C. The infrared and nuclear magnetic resonance spectra were in agreement with the proposed structure.

Analysis Calcd. for $C_{32}H_{50}ClNO_3$: C, 72.21; H, 9.47; N, 2.63. Found: C, 72.20; H, 9.56; N, 2.62.

EXAMPLE 3

4,4-Dimethyl-7-(3-methyl-2-octyl)-9-[3-(piperidino)propionyloxy]-1,2,3,4-tetrahydrocyclopenta[c][1]benzopyran hydrochloride

2.8 g. (8.2 mmoles) of 4,4-dimethyl-9-hydroxy-7-(3-methyl-2-octyl)-1,2,3,4-tetrahydrocyclopenta[c][1]benzopyran, 1.77 g. (8.6 mmoles) of dicyclohexylcarbodiimide and 1.65 g. (8.5 mmoles) of β-piperidinopropionic acid hydrochloride (m.p. 216°–220°C., J. Am. Chem. Soc. 73, 3168 (1951) were combined with 125 ml. of methylene chloride and stirred at room temperature for about 20 hours. The reaction mixture was filtered and the methylene chloride removed using a rotary evaporator. The residue was treated with benzene and filtered to remove a small quantity of insoluble material. The benzene was evaporated and the dark, viscous residue was chromatographed using 100 g. of 60–100 mesh activated magnesium silicate (Florisil) and methanol/chloroform graded solvent mixtures. Chromatography gave a small quantity of orange oil which was dissolved in ether and treated with a solution of ethereal HCl. The desired compound appeared as white crystals which were filtered and washed with additional ether. The colorless crystals (86 mg., m.p. 106°–107°C.) were pure by thin layer chromatography (10% MeOH/CHCl$_3$) and the nuclear magnetic resonance and infrared spectra were in agreement with the proposed structure.

Analysis Calcd. for $C_{31}H_{48}ClNO_3$: C, 71.85; H, 9.34; N, 2.70. Found: C, 71.72; H, 9.34; N, 2.77.

EXAMPLE 4

1-[4-(morpholino)butyryloxy]-3-n-pentyl-6,6,9-trimethyl-6a,7,8,10a-tetrahydrodibenzo[b,d]-pyran hydrochloride

0.7 g. (2.23 mmoles) of 1-Hydroxy-3n-pentyl-6,6,9-trimethyl-6a,7,8,10a-tetrahydrodibenzo[b,d]pyran, 0.48 g. (2.28 mmoles) of γ-morpholinobutyric acid hydrochloride (Cruickshank and Sheehan, J. Am. Chem. Soc. 83, 2891 (1961), m.p. 180°–182°C.) and 0.48 g. (2.35 mmoles) of dicyclohexylcarbodiimide were combined with 35 ml. of methylene chloride and stirred at room temperature for a total of 40 hours. The insoluble by-product of dicyclohexylurea was separated by filtration and the methylene chloride was removed using a rotary evaporator. The resulting residue was dissolved in about 20 ml. of benzene and a small amount of insoluble material was removed by filtration. The benzene was evaporated and the residue dried in vacuo to give 0.7 g. of fluffy, white material. Crystallization from benzene/petroleum ether gave 0.4 g. of product as colorless crystals, m.p. 99°–101°C. The material was pure by thin layer chromatography (10% MeOH/CHCl$_3$); the infrared and nuclear magnetic resonance spectra were in agreement with the proposed structure.

Analysis Calcd. for $C_{29}H_{44}ClNO_4·½H_2O$: C, 67.60; H, 8.81; N, 2.72. Found: C, 67.74; H, 8.68; N, 2.81.

EXAMPLE 5

4,4-Dimethyl-7-(3-methyl-2-octyl)-9-[4-(morpholino)butyryloxy]-1,2,3,4-tetrahydrocyclopenta[c][1]benzopyran hydrochloride 6.4 g. (18.7 mmole) of 4,4-Dimethyl-9-hydroxy-7-(3-methyl-2-octyl)-1,2,3,4-tetrahydrocyclopenta[c][1]benzopyran, 4.33 g. (21.0 mmoles) of dicyclohexylcarbodiimide and 4.26 g. (20.3 mmoles) of γ-morpholinobutyric acid hydrochloride were combined with 325 ml. of methylene chloride and stirred at room temperature for a total of 24 hours. The insoluble by-product of dicyclohexylurea was separated by filtration and the methylene chloride was removed using a rotary evaporator. The brown viscous residue was dissolved in about 100 ml. of benzene and the benzene solution was filtered to remove a small amount of insoluble material. The benzene was removed using a rotary evaporator and the remaining residue was triturated with approximately 250 ml. of ether. The solid which formed was filtered, washed with ether and dried to give 8.6 g. of beige solid. The material was crystallized from benzene/ether to give 3.5 g. of product as a colorless solid, m.p. 151°–153°C. The material was pure by thin layer chromatography (10% MeOH/CHCl$_3$); the infrared and nuclear magnetic resonance spectra were in agreement with the proposed structure. An additional 3.3 g. of somewhat impure material was recovered from the mother liquor.

Analysis Calcd. for $C_{31}H_{48}ClNO_4$: C, 69.70; H, 9.06; N, 2.62. Found: C, 69.43; H, 8.98; N, 2.55.

EXAMPLE 6

4,4-Dimethyl-9-[4-(morpholino)butyryloxy]-7n-pentyl-1,2,3,4-tetrahydroxycyclopenta[[c][1]benzopyran hydrochloride 1.0 g. (3.5 mmoles) of 4,4-dimethyl-9-hydroxy-7-n-pentyl-1,2,3,4-tetrahydrocyclopenta-[c][1]benzopyran, 0.76 g. (3.63 mmoles) of γ-morpholinobutyric acid hydrochloride and 0.76 g. (3.70 mmoles) of dicyclohexylcarbodiimide were combined in 75 ml. of methylene chloride and stirred at room temperature for 24 hours. The insoluble by-product of dicyclohexylurea was removed by filtration and the methylene chloride solution was concentrated to 20 ml. Cyclohexane was added until the desired compound was obtained as a colorless solid. Recrystallization from methylene chloride/cyclohexane gave 1.1 g. (65% yield) of product as colorless crystals, m.p. 181°–183°C. The material was pure by thin layer chromatography (5% MeOH/CHCl$_3$); the infrared and nuclear magnetic resonance spectra were consistent with the proposed structure.

Analysis Calcd. for $C_{27}H_{40}ClNO_4$: C, 67.83; H, 8.43; N, 2.93. Found: C, 67.75; H, 8.31; N, 2.90.

EXAMPLE 7

3n-pentyl-1-[4-(piperidino)butyryloxy]-6,6,9-trimethyl-6a,7,8,10a-tetrahydrodibenzo[b,d]pyran hydrochloride 0.46 g. (1.47 mmoles) of 1-Hydroxy-3-n-pentyl-6,6,9-trimethyl-6a,7,8,10a-tetrahydrodibenzo[b,d]pyran, 0.31 g. (1.47 mmoles) of γ-piperidinobutyric acid hydrochloride and 0.32 g. (1.55 mmoles) of dicyclohexylcarbodiimide were combined in 25 ml. of methylene chloride and stirred at room temperature for 4 hours. The insoluble by-product of dicyclohexylurea was removed by filtration and the methylene chloride was evaporated to give a gummy, yellowish residue. The gummy material was triturated several times with petroleum ether and dried in vacuo to give 350 mg. of product as a colorless foam-like solid. The sample was pure by thin-layer chromatography (10% MeOH/CHCl$_3$) and the infrared spectrum was consistent with the proposed structure.

EXAMPLE 8

γ-Pyrrolidinobutyric acid hydrochloride 30.0 g. (0.13 mole) of Methyl γ-iodobutyrate (Blicke et al., J. Am. Chem. Soc. 63, 2488 (1941)) was combined with 36 g. of pyrrolidine in 300 ml. of benzene, heated at 60°C. for 0.5 hour and stirred at room temperature for 16 hours. A dark orange layer formed. The benzene solution was decanted, concentrated and distilled (b.p. 100°C. at 15 mm Hg) to give 10 g. of colorless liquid. The infrared and nuclear magnetic resonance spectra indicated the product to be methyl γ-pyrrolidino-butyrate. This material was dissolved in 100 ml. of 18% hydrochloric acid and heated at reflux for 28 hours. The solution was concentrated under reduced pressure to give a semi-solid which was triturated with acetone and filtered. Recrystallization from acetic acid/acetone gave 8.3 g. (33%) of the desired acid hydrochloride as colorless crystals, m.p. 126°–127°C. The infrared and nuclear magnetic resonance spectra were consistent with the proposed structure.

Analysis Calcd. for $C_8H_{16}ClNO_2$: C, 49.601 H, 8.33; N, 7.28. Found: C, 49.79; H, 8.14; N, 7.21.

EXAMPLE 9

4,4-Dimethyl-7-(3-methyl-2-octyl)-9-[4-(pyrrolidino)-butyryloxy]-1,2,3,4-tetrahydrocyclopenta[c][1]benzopyran hydrochloride 3.21 g. (9.37 mmole) of 4,4-Dimethyl-9-hydroxy-7-(3-methyl-2-octyl)-1,2,3,4-tetrahydrocyclopenta[c][1]benzopyran was combined with 1.82 g. (9.37 mmole) of γ-pyrrolidinobutyric acid hydrochloride and 2.06 g. (10.0 mmole) of dicyclohexylcarbodiimide in 150 ml. of methylene chloride and stirred at room temperature for 2½ hours. The insoluble by-product of dicyclohexylurea was removed by filtration and the filtrate was evaporated to give a residue which crystallized upon standing. The material was triturated with ether and filtered. Recrystallization from benzene/ether gave 3.5 g. (72%) of product of colorless crystals, m.p. 138°–141°C. The material was pure by thin layer chromatography (10% MeOH/CHCl$_3$); the infrared and nuclear magnetic resonance spectra were consistent with the proposed structure.

Analysis Calcd. for $C_{31}H_{48}ClNO_3$: C, 71.85; H, 9.34; N, 2.70. Found: C, 71.91; H, 9.18; N, 2.81.

EXAMPLE 10

γ-Homopiperidinobutyric acid hydrochloride 23.0 g. (0.1 mmole) of Methyl γ-iodobutyrate (Blicke et al, J. Am. Chem. Soc. 63, 2488 (1941)) was combined with 25.0 g. (0.4 mole) of homopiperidine and heated at 70°C. for 3 hours. The precipitate of amine hydroiodide was removed by filtration and the filtrate was concentrated to an orange oil. The methyl γ-homopiperidinobutyrate distilled as 14.0 g. of colorless liquid at 0.5 mm., b.p. 70°–71°C. This material was dissolved in 75 ml. of aqueous 18% hydrochloric acid solution and heated at reflux for 16 hours. The solution was concentrated under reduced pressure to give a semi-solid residue which was trituruated with acetone and filtered. Recrystallization from acetic acid/acetone gave 10.0 g. (45%) of product as colorless crystals, m.p. 178°–179°C. The infrared and nuclear magnetic resonance spectra were consistent with the proposed structure.

Analysis Calcd. for $C_{10}H_{20}ClNO_2$: C, 54.20; H, 9.09; N, 6.32. Found: C, 54.21; H, 8.93; N, 6.26.

EXAMPLE 11

4,4-Dimethyl-9-[4-(homopiperidino)butyryloxy]-7-(3-methyl-2-octyl)-1,2,3,4-tetrahydrocyclopenta-[c][1]benzopyran hydrochloride 4.0 g. (11.7 mmole) of 4,4-Dimethyl-9-hydroxy-7-(3-methyl-2-octyl)-1,2,3,4-tetrahydrocyclopenta[c][1]benzopyran was combined with 2.6 g. (11.7 mmole) of γ-homopiperidinobutyric acid hydrochloride and 2.6 g. (12.5 mmole) of dicyclohexylcarbodiimide in 175 ml. of methylene chloride and stirred at room temperature for 3.5 hours. The dicyclohexylurea was separated by filtration and the methylene chloride was removed on a rotary evaporator. The residue was dissolved in a methylene chloride/cyclohexane mixture and the small amount of solid which appeared was removed by filtration. The solvents were evaporated to give a residue which crystallized from benzene/ether. Recrystallization gave 5.0 g. (78%) of product as colorless crystals, m.p. 150°–152.5°C. The sample was pure by thin layer chromatography (10% MeOH/CHCl$_3$) and the infrared and nuclear magnetic resonance spectra were consistent with the proposed structure.

Analysis Calcd. for $C_{33}H_{52}ClNO_3$: C, 72.45; H, 9.59; N, 2.56. Found: C, 72.57; H, 9.44; N, 2.58.

EXAMPLE 12

γ-Morpholinobutyric acid hydrobromide 15 g. (0.052 mole) of Methyl γ-morpholinobutyrate (Cruickshank and Sheehan, J. Am. Chem. Soc. 83, 2891 (1961)) was dissolved in a mixture of 45 ml. of 47% hydrobromic acid and 45 ml. of water and heated for 16 hours at reflux. The solution was taken to dryness under reduced pressure, and the solid which formed was triturated with acetone. The material was filtered and crystallized from 60 ml. of acetic acid to give 12.4 g. (95%) of product as colorless crystals, m.p. 151°–152.5°C. The infrared and nuclear magnetic resonance spectra were consistent with the proposed structure.

Analysis Calcd. for $C_8H_{16}BrNO_3$: C, 37.81; H, 6.36; N, 5.51. Found: C, 37.80; H, 6.28; N, 5.47.

EXAMPLE 13

1-[4-(Morpholino)butyryloxy]-3-n-pentyl-6,6,9-trimethyl-6a,7,8,10a-tetrahydrodibenzo[b,d]pyran hydrobromide 3.54 g. (11.27 mmole) of 1-Hydroxy-3-n-pentyl-6,6,9-trimethyl-10a,6a,7,8-tetrahydrodibenzo[b,d]pyran, 2.86 g. (11.27 mmole) of γ-morpholinobutyric acid hydrobromide and 2.50 g. (12.12 mole) of dicyclohexylcarbodiimide were combined in 200 ml. of methylene chloride and stirred at room temperature for 24 hours. The reaction mixture was cooled and the by-product of dicyclohexylurea was removed by filtration. The volume of methylene chloride was reduced and 25 ml. of cyclohexane was added. The mixture was cooled and the small amount of solid which formed was removed by filtration. All solvents were removed on a rotary evaporation and the residue was dried in vacuo. The resulting foamy material was dissolved in a mixture of benzene and ether and placed in cold storage to yield 3.0 g. (50%) of product as colorless crystals, m.p. 103°–105°C. The compound gave a R$_f$ 0.5 in 5% MeOH/CHCl$_3$. The infrared and nuclear magnetic resonance spectra were consistent with the proposed structure.

Analysis Calcd. for $C_{29}H_{44}BrNO_4 \cdot \frac{1}{2}H_2O$: C, 62.20; H, 8.10; N, 2.50. Found: C, 62.30; H, 7.95; N, 2.68.

EXAMPLE 14

3-(3-Methyl-2-octyl)-1-[4-(morpholino)butyryloxy]-6,6,9-trimethyl-7,8,9,10-tetrahydro-6H-dibenzo[b,d]-pyran hydrobromide 4.12 g. (11.15 mmole) of 1-Hydroxy-3-(3-methyl-2-octyl)-6,6,9-trimethyl-7,8,9,10-tetrahydro-6H-dibenzo[b,d]pyran was combined with 2.84 g. (11.15 mmole) of γ-morpholinobutyric acid hydrobromide and 2.48 g. (12.0 mmole) of dicyclohexylcarbodiimide in 250 ml. of methylene chloride and stirred at room temperature for 16 hours. The by-product of dicyclohexylurea was removed by filtration and the filtrate was evaporated to give a golden, viscous residue. The material was dissolved in ether and the solid which appeared was removed by filtration. Recrystallization from benzene/ether gave 2.8 g. (41%) of product as colorless crystals, m.p. 120°–122°C. The compound showed an R$_f$ 0.7 in 10% MeOH/CHCl$_3$; the infrared and nuclear magnetic resonance spectra were consistent with the proposed structure.

Analysis Calcd. for $C_{33}H_{52}BrNO_4$: C, 65.34; H, 8.64; N, 2.27. Found: C, 65.47, H, 8.63; N, 2.49.

EXAMPLE 15

3-(3-Methyl-2-octyl)-1-[4-(piperidino)butyryloxy]-6,6,9-trimethyl-7,8,9,10-tetrahydro-6H-dibenzo[b,d]-pyran hydrochloride 2.5 g. (6.76 mmole) of 1-Hydroxy-3-(3-methyl-2-octyl)-6,6,9-trimethyl-7,8,9,10-tetrahydro-6H-dibenzo[b,d]pyran was combined with 1.41 g. (6.76 mmole) of γ-piperidinobutyric acid hydrochloride and 1.48 g. (7.16 mmole) of dicyclohexylcarbodiimide in 125 ml. of methylene chloride and stirred at room temperature for 16 hours. The by-product of dicyclohexylurea was removed by filtration and the filtrate was evaporated to give a light brown residue. The residue was dissolved in ether and the small amount of solid which appeared was removed by filtration. The ether was removed on a rotary evaporator and the gummy residue which remained was triturated several times with small quantities of hexane. The material was thoroughly dried to give 2.8 (74%) of product as a colorless powder. The material was pure by thin layer chromatography (10% MeOH/CHCl$_3$); the infrared and nuclear magnetic resnance spectra were consistent with the desired product.

Analysis Calcd. for $C_{34}H_{54}ClNO_3$: C, 72.89; H, 9.71; N, 2.50. Found: C, 72.36; H, 9.58; N, 2.67.

EXAMPLES 16–19

The following compounds are prepared according to the method of Example 2 by reacting the appropriate acid with the corresponding benzopyran and dicyclohexylcarbodiimide:

4,4-Dimethyl-7-(3-methyl-2-octyl)-9-[5-(piperidino)-valeryloxy]-1,2,3,4-tetrahydrocyclopenta[c][1]benzopyran from 4,4-dimethyl-9-hydroxy-7-(3-methyl-2-octyl)-1,2,3,4-tetrahydrocyclopenta[c][1]benzopyran and δ-piperidinovaleric acid.

4,4-Dimethyl-7-n-hexyl-9-(morpholinoacetyloxy)-1,2,3,4-tetrahydrocyclopenta[c][1]benzopyran tosylate from 4,4-dimethyl-7-n-hexyl-9-hydroxy-1,2,3,4-tetrahydrocyclopenta[c][1]benzopyran and morpholinoacetic acid tosylate.

9-[4-Azetidino butyryloxy]-4,4,7-trimethyl-1,2,3,4-tetrahydrocyclopenta[c][1]benzopyran tartrate from 9-hydroxy-4,4,7-trimethyl-1,2,3,4-tetrahydrocyclopenta[c][1]benzopyran and γ-azetidinobutyric acid tartrate.

4,4-Dimethyl-7-(2-tetradecyl)-9-[8-(thiomorpholino)-octanoyloxy]-1,2,3,4-tetrahydrocyclopenta[c][1]benzopyran from 4,4-dimethyl-9-hydroxy-7-(2-tetradecyl)-1,2,3,4-tetrahydrocyclopenta[c][1]benzopyran and thiomorpholinooctanoic acid.

EXAMPLE 20

4,4-Dimethyl-9-[4-(homopiperidino)butyryloxy]-7-pentyl-1,2,3,4-tetrahydrocyclopenta[c][1]benzopyran hydrochloride 1.0 g. (3.5 mmole) of 4,4-dimethyl-9-hydroxy-7-pentyl-1,2,3,4-tetrahydrocyclopenta[c][1]benzopyran was combined with 0.77 g. (3.5 mmole) of γ-homopiperidinobutyric acid hydrochloride and 0.77 g. (3.7 mmole) of dicyclohexylcarbodiimide in 50 ml. of methylene chloride and stirred for 16 hours at room temperature. The byproduct of dicyclohexylurea was removed by filtration, and the filtrate was evaporated to give a golden, gummy residue. This residue was dissolved in a combination of 20 ml. methylene chloride/20 ml. cyclohexane and allowed to stand at 0°C for 16 hours. A small quantity of solid appeared and this was separated by filtration. Evaporation of the solvents gave a semi-solid residue which was triturated with ether, filtered and dried. The material recrystallized from 15 ml. methylene chloride/45 ml. ethyl ether to give 1.22 g. (71%) of colorless crystals, m.p. 187°–88°C. The sample showed a single spot on thin layer chromatography (10% MeOH/CHCl$_3$) and the infrared and nuclear magnetic resonance spectra confirmed the structure.

Analysis Calcd. for C$_{29}$H$_{44}$ClNO$_3$ (MW = 490.10): C, 71.05; H, 9.05; N, 2.86. Found: C, 70.85; H, 8.89; N, 2.75.

EXAMPLE 21

4,4-Dimethyl-9-[pyrrolidino)butyryloxy]-7-pentyl-1,2,3,4-tetrahydrocyclopenta[c][1]benzopyran hydrochloride A mixture of 1.0 g. (3.5 mmole) of 4,4-dimethyl-9-hydroxy-7-pentyl-1,2,3,4-tetrahydrocyclopenta[c][1]benzopyran, 0.68 g. (3.5 mmole) of γ-pyrrolidinobutyric acid hydrochloride and 0.77 g. (3.7 mmole) of dicyclohexylcarbodiimide in 60 ml. of methylene chloride was stirred at room temperature for 4 hours. After standing for 16 hours at 0°C, the byproduct of dicyclohexylurea was removed by filtration, and the filtrate was evaporated to give a gummy yellow residue. This residue was dissolved in a combination of of 10 ml. methylene chloride/10 ml. cyclohexane and cooled for 2 hours. After removal by filtration of a small amount of solid, the solvents were distilled off using a rotary evaporator. The compound crystallized from 50 ml. of diethyl ether and it was filtered and dried. Recrystallization from 6 ml. benzene/30 ml. diethyl ether gave 1.05 g. (65%) of colorless crystals, m.p. 137°–41°C. The sample was pure by thin layer chromatography (10% MeOH/CHCl$_3$) and the infrared and nuclear magnetic resonance spectra were in agreement with the proposed structure.

Analysis Calcd. for C$_{27}$H$_{40}$ClNO$_3$ (MW = 462.05): C, 70.18; H, 8.72; N, 3.03. Found: C, 69.95; H, 8.65; N, 3.07.

EXAMPLE 22

1-[4-Homopiperidino)butyryloxy]-3-(3-methyl-2-octyl)-6,6,9-trimethyl-7,8,9,10-tetrahydro-6H-dibenzo[b,d]pyran 3.1 g. (8.4 mmole) of 1-hydroxy-3-(3-methyl-2-octyl)-6,6,9-trimethyl-7,8,9,10-tetrahydro-6H-dibenzo[b,d]pyran was combined with 1.86 g. (8.4 mmole) of γ-homopiperidinobutyric acid hydrochloride and 1.85 g. (9.0 mmole) of dicyclohexylcarbodiimide in 150 ml. of methylene chloride and stirred at room temperature for 16 hours. The reaction mixture was cooled and the byproduct of dicyclohexylurea was removed by suction filtration. The solvent was evaporated to give a residue which was chromatographed using magnesium silicate (60–100 mesh) and graded methanol/chloroform solvent mixtures. The fractions were monitored by thin layer chromatography, and the desired material was obtained from the 5% MeOH/CHCl$_3$ fractions. The appropriate fractions were combined, and evaporated to give 1.78 g. (40%) of a yellow gum. The material was pure by thin layer chromatography (10% MeOH/CHCl$_3$), and the infrared and nuclear magnetic resonance spectra were consistent with the proposed structure.

Analysis Calcd. for C$_{35}$H$_{55}$NO$_3$ (MW = 537.79): C, 78.16; H, 10.31; N, 2.60; Found: C, 78.07; H, 10.44; N, 2.79.

EXAMPLE 23

3-(3-Methyl-2-octyl)-1-[4-(morpholino)butyryloxy]-6,6,9-trimethyl-6a,7,10,10a-tetrahydrodibenzo[b,d]pyran 2.44 g. (6.6 mmole) of 1-hydroxy-3-(3-methyl-2-octyl)-6,6,9-trimethyl-6a,7,10,10a-tetrahydrodibenzo[b,d]pyran was combined with 1.37 g. (6.6 mmole) of γ-morpholinobutyric acid hydrochloride and 1.42 g. (6.9 mmole) of dicyclohexylcarbodiimide in 170 ml. of methylene chloride and stirred at room temperature for 6 hours. The reaction mixture was cooled, and the byproduct of dicyclohexylurea was removed by suction filtration. The solvent was evaporated to give a yellow, foamy residue which was chromatographed using magnesium silicate (60–100 mesh) and graded methanol/chloroform solvent mixtures. The desired material was obtained from the 2% methanol/chloroform fractions, and the appropriate fractions were combined and evaporated to give 1.76 g. (51%) of a light yellow gum. The sample was pure by thin layer chromatography (5% MeOH/CHCl$_3$), and the infrared and nuclear magnetic resonance spectra confirmed the proposed structure. An aliquot of the material was converted to the hydrochloride salt by addition of ethereal hydrogen chloride to a diethyl ether solution of the ester.

Analysis Calcd. for $C_{33}H_{51}NO_4$ (MW = 525.73): C, 75.39; H, 9.78; N, 2.66. Found: C, 75.57; H, 9.59; N, 2.70.

EXAMPLE 24

9-hydroxy-7-(3-methyl-2-octyl)-1,4,4-trimethyl-1,2,3,4-tetrahydrocyclopenta[c][1]benzopyran To 60 ml. of benzene and 4.3 ml. of phosphorous oxychloride was added 14 g. of 5-(3-methyl-2-octyl)-resorcinol and 11 g. of 5-methyl-2-carbethoxycyclopentanone [J. Org. Chem. 29, 2782 (1964)]. The solution was refluxed 13 hours and let stand at room temperature for 10 hours. Dilute sodium carbonate was then added with stirring. The reaction mixture was extracted with ether, the ether solution was dried over magnesium sulfate and then concentrated to a dark oil. The dark oil was extracted twice with pentane leaving 10.4 g. of 1-methyl-4-oxo-9-hydroxy-7-(3-methyl-2-octyl)-1,2,3,4-tetrahydrocyclopenta[c][1]benzopyran.

A methyl magnesium bromide solution was prepared by adding a solution of 175 g. of methylbromide in 450 ml. of ether dropwise to 40 g. of magnesium in 150 ml. of ether. To the solution was added 53 g. of 1-methyl-4-oxo-9-hydroxy-7-(3-methyl-2-octyl)-1,2,3,4-tetrahydrocyclopenta[c][1]benzopyran in 90 ml. of benzene and 90 ml. of ether. The mixture was refluxed for 18 hours. The mixture was cooled and then 800 ml. of saturated aqueous ammonium chloride was added very slowly. The organic phase was separated, dried over magnesium sulfate and concentrated to a residue. The residue was dissolved in 900 ml. of benzene and 0.1 g. of p-toluenesulfonic acid was added. The mixture was refluxed for 2.5 hours, then cooled and shaken with aqueous potassium bicarbonate. The solvent was removed by evaporation. Petroleum ether and activated charcoal were added, the solution was filtered and then concentrated to give 45 g. of crude oil. The product was purified by chromatography on magnesium silicate using 95/5 petroleum ether/ether as the eluting solvent given 25 g. of 9-hydroxy-7-(3-methyl-2-octyl)-1,4,4-trimethyl-1,2,3,4-tetrahydrocyclopenta[c][1]benzopyran.

EXAMPLE 25

7-(3-methyl-2-octyl)-9-[4-(piperidino)-butyryloxy]-1,4,4-trimethyl-1,2,3,4-tetrahydrocyclopenta[c][1-]benzopyran hydrochloride 9-hydroxy-7-(3-methyl-2-octyl)-1,4,4-trimethyl-1,2,3,4-tetrahydrocyclopenta[c][1]benzopyran from Example 24 is reacted with γ-piperidinobutyric acid hydrochloride following the procedure of Example 2 to form 7-(3-methyl-2-octyl)-9[4-(piperidino)-butyryloxy]-1,4,4-trimethyl-1,2,3,4-tetrahydrocyclopenta[c][1-]benzopyran hydrochloride.

EXAMPLE 26

9-Hydroxy-7-(3-methyl-2-octyl)-2,4,4-trimethyl-1,2,3,4-tetrahydrocyclopenta[c][1]benzopyran To 300 ml. of benzene was added 26 g. of sodium hydride with stirring under nitrogen. The sodium hydride settled and 220 ml. of benzene was withdrawn. Then 300 ml. of fresh benzene was added. The reaction mixture was refluxed and to it was added 47 g. of the diethyl ester of 3-methyladipic acid in 50 ml. of benzene dropwise. After ¼ was added, 75 ml. of benzene was distilled off at atmospheric pressure after addition of part of the diethyl ester to induce reaction. The reaction then proceeded quickly. The rest of the diester was added dropwise. Then 150 ml. of benzene was added and the mixture was cooled in ice. Then 45 ml. of acetic acid was added dropwise with hydrogen evolution. To the resulting pasty mass was added 100 ml. of water. The aqueous layer was extracted with benzene, dried and the combined organic layers were distilled under vacuum to give 32.1 g. of 2-carboethoxy-4-methyl cyclopentanone.

To 70 ml. of benzene was added 15 g. of 5-(3-methyl-2-octyl)-resorcinol, 14 g. of 2-carboethoxy-4-methyl cyclopentanone and 10 g. of phosphorous oxychloride followed by refluxing for 8.5 hours. After standing for 8 hours at room temperature the red solution was poured into cold dilute sodium carbonate and then extracted with ether. The ether layer was dried and concentrated and then pentane was added to give a gummy blue solid. This was recrystallized from acetonitrile to give 7.5 g. of 2-methyl-4-oxo-9-hydroxy-7-(3-methyl-2-octyl)-1,2,3,4-tetrahydrocyclopenta[c][1-]benzopyran as a light blue solid, m.p. 176–178°C.

A solution of 45 g. of methylbromide in 180 ml. of ether was added dropwise to 10 g. of magnesium in 70 ml. of ether over a period of 40 minutes followed by refluxing for 0.5 hours. 50 ml. of ether was boiled off. Then to the solution was added dropwise a suspension of 12.6 g. of 2-methyl-4-oxo-9-hydroxy-7-(3-methyl-2-octyl)-1,2,3,4-tetrahydrocyclopenta[c][1]benzopyran in 60 ml. of ether and 60 ml. of benzene. The mixture was refluxed for 20 hours. Then 250 ml. of saturated aqueous ammonium chloride was added dropwise very slowly. The reaction mixture was extracted with ether, dried over magnesium sulfate and evaporated to a residue. The residue was dissolved in 300 ml. of benzene, 0.05 g. of p-toluene sulfonic acid was added and the mixture was refluxed for 2 hours. The mixture was cooled, shaken with sodium bicarbonate, and dried over magnesium sulfate. The mixture was added to petroleum ether and treated with charcoal. The mixture was chromatographed using 95/5 petroleum ether/ether for elution. The product 9-hydroxy-7-(3-methyl-2-octyl)-2,4,4-trimethyl-1,2,3,4-tetrahydrocyclopenta[c][1]benzopyran was obtained as 10.95 g. of yellow oil.

EXAMPLE 27

7-(3-Methyl-2-octyl)-9-[3-(piperidino)-propionyloxy]-2,4,4-trimethyl-1,2,3,4-tetrahydrocyclopenta[c][1]-benzopyran hydrochloride 9-Hydroxy-7-(3-methyl-2-octyl)-2,4,4-trimethyl-1,2,3,4-tetrahydrocyclopenta[c][1]benzopyran from Example 26 is reacted with β-piperidinopropionic acid hydrochloride following the procedure of Example 3 to produce 7-(3-methyl-2-octyl-9-[3-(piperidino)-propionyloxy]-2,4,4-trimethyl-1,2,3,4-tetrahydrocyclopenta[c][1]-benzopyran hydrochloride.

EXAMPLE 28

9-Hydroxy-7-(3-methyl-2-octyl)-2,2,4,4-tetramethyl-1,2,3,4-tetrahydrocyclopenta[c][1]benzopyran to 13.5 g. of 5-(3-methyl-2-octyl)-resorcinol and 10.5 g. of 4,4-dimethyl-2-carboethoxycyclopentanone

[Canadian J. of Chem. 47, 1982–1988 (1969)] in 59 ml. of benzene was added 4.3 ml. of phosphorus oxychloride with stirring and refluxing for 6 hours. The red solution was let stand at room temperature for 8 hours, poured into ice and sodium carbonate solution. The colorless mixture was extracted with ether, dried over magnesium sulfate and concentrated. The mixture was extracted with cold pentane and the pentane was discarded. The residue [9-hydroxy-7-(3-methyl-2-octyl)-2,2-dimethyl-4-oxo-1,2,3,4-tetrahydrocyclopenta[c][1]benzopyran] was obtained as a gummy solid.

22 grams of magnesium was added to 100 ml. of ether and to the mixture was added dropwise a solution of 124 g. of methyliodide in 100 ml. of ether. The mixture was refluxed for 0.5 hour and then the crude 9-hydroxy-7-(3-methyl-2-octyl)-2,2-dimethyl-4-oxo-1,2,3,4-tetrahydrocyclopenta[c][1]benzopyran in 130 ml. of benzene was added over 20 minutes. The mixture was refluxed and stirred 18 hours. The mixture was cooled and 50 ml. of water was added dropwise under nitrogen. Then 35 ml. of sulfuric acid and 150 ml. of water were slowly added. The ether layer was dried over magnesium sulfate and concentrated to a residue which was dissolved in 200 ml. of benzene. Then 250 mg. of p-toluene sulfonic acid was added followed by refluxing for 1 hour. The solvent was removed and the residue was dissolved in pentane. The solution was treated with charcoal, filtered and concentrated to 13.5 g. of 9-hydroxy-7-(3-methyl-2-octyl)-2,2,4,4,-tetramethyl-1,2,3,4-tetrahydrocyclopenta[c][1]benzopyran as a dark oil 90–95% pure. The product was purified by column chromatography to give 10.4 of pure product.

EXAMPLE 29

7-(3-Methyl-2-octyl)-9-[4-morpholino)-butyryloxy]-2,2,4,4-tetramethyl-1,2,3,4-tetrahydrocyclopenta[c][1] benzopyran hydrochloride 9-Hydroxy-7-(3-methyl-2-octyl)-2,2,4,4-tetramethyl-1,2,3,4-tetrahydrocyclopenta[c][1]benzopyran from Example 28 is reacted with γ-morpholinobutyric acid hydrochloride following the procedure of Example 4 to produce 7-(3-methyl-2-octyl)-9-[4-morpholino)-butyryloxy]-2,2,4,4-tetramethyl-1,2,3,4-tetrahydrocyclopenta[c][1]benzopyran hydrochloride.

EXAMPLE 30

1-Ethyl-4,4-dimethyl-9-hydroxy-7-(3-methyl-2-octyl)-1,2,3,4-tetrahydrocyclopenta[c][1]benzopyran The general procedure of Example 24 is followed in the following reactions.

2-Carboethoxycyclopentanone is reacted with ethyl iodide in the presence of sodium hydride to produce 2-carboethoxy-2-ethyl-cyclopentanone.

2-Carboethoxy-2-ethyl-cyclopentanone is reacted with sodium ethoxide to produce 2-ethyl-5-carboethoxycyclopentanone. (J. Org. Chem. 29, 2782 (1964))

2-Carboethoxy-2-ethyl-cyclopentanone is reacted with 5-(3-methyl-2-octyl)-resorcinol to produce 1-ethyl-4-oxo-9-hydroxy-7-(3-methyl-2-octyl)-1,2,3,4-tetrahydrocyclopenta[c][1]benzopyran.

A solution of 40.1 g. (0.112 mole) of 1-ethyl-4-oxo-9-hydroxy-7-(3-methyl-2-octyl)-1,2,3,4-tetrahydrocyclopenta[c][1]benzopyran in 300 ml. of ether was added dropwise to a stirred solution of 1.12 mole of methyl magnesium bromide in 340 ml. of ether. The resulting solution was stirred and refluxed for 19 hours.

The reaction mixture was cooled to room temperature and to the mixture with stirring was added dropwise an ammonium chloride solution (120 g. in 350 ml. of water). The mixture was filtered to remove the inorganic salts which were washed well with benzene. The filtrate was concentrated to dryness to give a dark viscous oil which was taken up in 200 ml. of benzene. A few crystals of p-toluenesulfonic acid monohydrate was added. The mixture was refluxed 2 hours using a water take off head. Only a trace of water was liberated. The solvents were removed giving 1-ethyl-4,4-dimethyl-9-hydroxy-7-(3-methyl-2-octyl)-1,2,3,4-tetrahydrocyclopenta[c][1]benzopyran as a dark viscous oil. The product was chromatographed on a magnesium silicate column and eluted with 96/4 petroleum ether/diethyl ether. After rechromatography there was obtained 8.1 g. of product. The nuclear magnetic resonance and infrared analysis of the product showed it to be the expected compound.

Analysis calcd. for $C_{25}H_{38}O_2$: C, 81.03; H, 10.34; O, 8.63. Found: C, 80.48; H, 10.36; O, 9.4.

EXAMPLE 31

1-Ethyl-4,4-dimethyl-7-(3-methyl-2-octyl)-9-[4-morpholino)butyryloxy]-1,2,3,4-tetrahydrocyclopenta[c][1]benzopyran hydrochloride 1-Ethyl-4,4-dimethyl-9-hydroxy-7-(3-methyl-2-octyl)-1,2,3,4-tetrahydrocyclopenta[c][1]benzopyran from Example 30 is reacted with γ-morpholinobutyric acid hydrochloride following the procedure of Example 5 to produce 1-ethyl-4,4-dimethyl-7-(3-methyl-2-octyl)-9-[4-morpholino)butyryloxy]-1,2,3,4-tetrahydrocyclopenta[c][1]benzopyran hydrochloride.

EXAMPLE 32

1-Hydroxy-3-(3-methyl-2-octyl)-7,8,9,10-tetrahydro-6,6,10-trimethyl-6H-dibenzo[b,d]pyran a. Ethyl (and Methyl) 3-methyl-2-oxocyclohexanecarboxylate A solution of 51.1 g. of the methyl and ethyl esters of 2-oxocyclohexanecarboxylic acid (0.311 mole) in 100 ml. of dry toluene was added to a suspension of 14.4 g. of sodium hydride (57% oil dispersion) in 300 ml. of dry toluene, with mechanical stirring and cooling to keep the reaction temperature at 10°–15°C. The addition took 30 min., after which the ice bath was removed and the reaction mixture was allowed to stand overnight at room temperature. The reaction mixture was then heated at 70°–75°C and stirred while a solution of 46.8 g. (0.33 mole) of methyl iodide in 50 ml. of dry toluene was added. After 4 hr. of heating and stirring thin layer chromatography (1:4 ethyl acetate/hexane) showed the reaction was complete.

The excess sodium hydride was decomposed by the addition of methanol, and the alkali was removed by washing with dilute hydrochloric acid. The excess acid was washed out, and the organic layer was dried over anhydrous sodium sulfate.

The rearrangement was effected by addition of 17.9 (0.33 mole) of sodium methoxide to the toluene solution of the 1-methyl-2-oxocyclohexanecarboxylic acid esters at room temperature, followed by heating at 100°C for 2.5 hr. The dark red solution was then kept cold (15°–20°C) while 40 ml. of water was carefully added, followed by 60 ml. of 1:1 hydrochloric acid and 100 ml. of water. The organic layer was separated, washed with water and with saturated sodium chloride solution, dried, and concentrated. The dark orange residual liquid was distilled at reduced pressure to give 32.6 g. (59%) of ethyl (and methyl) 3-methyl-2-oxocyclohexanecarboxylate, as a pale yellow-green liquid, b.p. 59°–72°C./0.1 mm. The structure of the liquid was confirmed by its nuclear magnetic resonance.

b. 1-Hydroxy-10-methyl-3-(3-methyl-2-octyl)-6-oxo-7,8,9,10-tetrahydro-6H-dibenzo[b,d]pyran A solution of 10.5 g. (0.06 mole) of ethyl (and methyl) 3-methyl-2-oxocyclohexanecarboxylate and 14.2 g. (0.06 mole) of 5-(3-methyl-2-octyl)-resorcinol in 240 ml. of benzene was dried by azeotropic distillation, and then 6.8 ml. (11.3 g., 0.074 mole) of phosphorus oxychloride was added. After refluxing for 72 hours, the solvent, excess phosphorus oxychloride, and generated hydrogen chloride were removed at reduced pressure, and the residue was diluted with 150 ml. of diethyl ether. The solution was treated first with sodium bicarbonate solution followed by potassium carbonate to insure complete hydrolysis of phosphate esters. Hydrochloric acid was added and the dark red organic layer was separated, washed with sodium chloride solution, dried and concentrated in a rotary evaporator. The dark red syrupy residue was triturated with petroleum ether, and the insoluble residue was dissolved in benzene and filtered. Concentration in a rotary evaporator left 21.8 g. of crude pyrone as a dark red resin. The product was purified and isolated by column chromatography on magnesium silicate with graded diethylether/petroleum ether as eluant.

The desired pyrone was found in the fractions eluted with late volumes of 15:85 diethylether/petroleum ether and with 35:65 diethylether/petroleum ether. Upon standing, these fractions crystallized to give 8.7 g. (40%) of sticky colorless solid, m.p. 108°–110°C. Nuclear magnetic resonance and infrared spectra and thin layer chromatography 1:4 ethyl acetate/hexane) showed the solid to be the desired pyrone, m.p. 108°–110°C.; 8.7 g. (40% yield).

c. 1-Hydroxy-3-(3-methyl-2-octyl)-7,8,9,10-tetrahydro-6,6,10-trimethyl-6H-dibenzo[b,d]pyran A solution of 8.30 g. (0.0232 mole) of 1-hydroxy-10-methyl-3-(3-methyl-2-octyl)-6-oxo-7,8,9,10-tetrahydro-6H-dibenzo[b,d]pyran in 60 ml. of anhydrous diethyl ether was added to a cooled solution of methyl magnesium bromide in 150 ml. of anhydrous diethyl ether, prepared from 6.8 g. (0.28 mole) of magnesium shavings by bubbling in gaseous methyl bromide until the metal had dissolved. The solution was allowed to warm to room temperature and stand 16 hr. The solution was then heated at reflux for 30 min., cooled in ice, and treated with a solution of methanol and 7 ml. of 1:1 hydrochloric acid, followed by 50 ml. of 1:1 hydrochloric acid and finally 70 ml. of water. The dark red-orange ether layer was separated, washed with water and saturated sodium chloride solution, dried, and concentrated. The intermediate triol, as a reddish residue, was the principal product at this stage.

The intermediate was dehydrated to the pyran by dissolving in 25 ml. of warm methanol, addition of 3 drops of concentrated hydrochloric acid, and heating on a hot water bath for 5 min. The red-orange solution was concentrated in a rotary evaporator and the residue was taken up in diethyl ether, washed with water, dried and again concentrated in a rotary evaporator. The residue of viscous liquid (9.5 g.) darkened on standing.

The pyran was purified and isolated by column chromatography on magnesium silicate, with petroleum ether and 1:99 diethyl ether/petroleum ether as eluant. From two reactions, using a total of 10.3 g. of pyrone, 8.6 g. (82%) of pyran was recovered as a colorless syrup that soon began to darken in air. Upon standing, the sample crystallized to a sticky colorless solid, m.p. about 65°–70°C.

Analysis Calcd. for $C_{25}H_{38}O_2$: C, 81.02; H, 10.34. Found: C, 80.18; H, 10.41.

The nuclear magnetic resonance and infrared spectra agreed with the assigned structure.

EXAMPLE 33

3-(3-Methyl-2-octyl)-1-[4-(pyrrolidino)-butyryloxy]-7,8,9,10-tetrahydro-6,6,10-trimethyl-6H-dibenzo[b,d]pyran hydrochloride 1-Hydroxy-3-(3-methyl-2-octyl)-7,8,9,10-tetrahydro-6,6,10-trimethyl-6H-dibenzo[b,d]pyran from Example 32 is reacted with γ-pyrrolidinobutyric acid hydrochloride following the procedure of Example 9 to produce 3-(3-methyl-2-octyl)-1-[4-(pyrrolidino)-butyryloxy]-7,8,9,10-tetrahydro-6,6,10-trimethyl-6H-dibenzo[b,d]pyran hydrochloride.

EXAMPLE 34

4,4-Dimethyl-9-[4-(thiomorpholino)butyryloxy]-7-(3-methyl-2-octyl)-1,2,3,4-tetrahydrocyclopenta[c][1]benzopyran hydrochloride A. Methyl γ-Thiomorpholinobutyrate A mixture of 64.0 g. (0.28 mole) of methyl γ-iodobutyrate, 28.0 g. (0.28 mole) of triethylamine, 28.7 g. (0.28 mole) of thiomorpholine (J. Am. Chem. Soc. 76, 1187 (1954)) and 1 liter of benzene was stirred and heated at 60°–70°C. for 18 hours. After cooling the reaction mixture, the precipitated amine hydroiodide was removed by suction filtration. The benzene solution was evaporated to give a orange-red residue which was vacuum distilled (b.p. 84°–85°C. at 0.1 mm) to give 28.38 g. (50%) of the product as a colorless liquid.

B. γ-Thiomorpholinobutyric acid hydrochloride

A solution of 28.0 g. (0.138 mole) of methyl γ-thiomorpholinobutyrate in 300 ml. of concentrated hydrochloric acid and 250 ml. of water was stirred and heated at reflux for 18 hours. The solvents were removed on a rotary evaporator to give a colorless residue which crystallized upon trituration with acetone. The solid was filtered, washed with acetone, and dried in vacuo to give 28.2 g. (91%) of the desired product as colorless crystals, m.p. 242°–245°C.

C. 4,4-Dimethyl-9-[4-(thiomorpholino)butyryloxy]-7-(3-methyl-2-octyl)-1,2,3,4-tetrahydrocyclopenta[c][1]benzopyran hydrochloride A mixture of 1.5 g. (4.4 mmole) of 4,4-dimethyl-9-hydroxy-7-(3-methyl-2-octyl)-1,2,3,4-tetrahydrocyclopenta[c][1]benzopyran, 0.99 g. (4.4 mmole) of γ-thiomorpholinobutyric acid hydrochloride, and 0.99 g. (4.8 mmole) of dicyclohexylcarbodiimide in 125 ml. of methylene chloride was stirred and heated at reflux for 16 hours. The reaction mixture was cooled and the byproduct of dicyclohexylurea was removed by suction filtration. The solvents were evaporated to give a residue which crystallized from a mixture of 10 ml. chloroform/40 ml. diethyl ether to give 0.85 g. (35%) of the desired product as a beige solid, m.p. 167°–171°C. The material was pure by thin layer chromatography, and the infrared and nuclear magnetic resonance spectra were in agreement with the proposed structure.

Analysis Calcd. for $C_{31}H_{48}ClNO_3S$ (MW = 550.15): C, 67.67; H, 8.79; N, 2.54. Found: C, 67.49; H, 8.89; N, 2.57.

EXAMPLE 35

1-[4-(Thiomorpholino)butyryloxy]-3-(3-methyl-2-octyl)-6,6,9-trimethyl-7,8,9,10-tetrahydro-6H-dibenzo[b,d]pyran A mixture of 4.0 g. (10.8 mmole) of 1-hydroxy-3-(3-methyl-2-octyl)-6,6,9-trimethyl-7,8,9,10-tetrahydro-6H-dibenzo[b,d]pyran, 2.4 g. (10.8 mmole) of γ-thiomorpholinobutyric acid hydrochloride, 2.38 g. (11.5 mmole) of dicyclohexylcarbodiimide and 250 ml. of methylene chloride was stirred and heated at reflux for 18 hours. After cooling the reaction mixture, the byproduct of dicyclohexylurea was removed by suction filtration. The solvent was evaporated to give a red-brown residue which was chromatographed using 90 g. of activated magnesium silicate (60–100 mesh) and chloroform as the solvent system. The fractions were monitored by thin layer chromatography, and the appropriate fractions were combined and evaporated to give 1.0 g. of a light yellow oil. The material was pure by thin layer chromatography, and the infrared and nuclear magnetic resonance spectra were in agreement with the designated structure.

Analysis Calcd. for $C_{33}H_{51}NO_3S$ (MW = 541.73): C, 73.16; H, 9.49; N, 2.58. Found: C, 73.13; H, 9.40; N, 2.50.

EXAMPLE 36

3-(3-Methyl-2-octyl)-1-[4-(morpholino)butyryloxy]-7,8,9,10-tetrahydro-6,6,10-trimethyl-6H-dibenzo[b,d]pyran A mixture of 1.66 g. (4.5 mmole) of 1-hydroxy-3-(3-methyl-2-octyl)-7,8,9,10-tetrahydro-6,6,10-trimethyl-6H-dibenzo[b,d]pyran, 0.94 g. (4.5 mmole) of γ-morpholinobutyric acid hydrochloride, 1.0 g. (4.75 mmole) of dicyclohexylcarbodiimide and 80 ml. of methylene chloride was stirred at room temperature for 19 hours. The reaction mixture was cooled and the byproduct of dicyclohexylurea was removed by filtration. The solvent was evaporated to give a golden, foamy residue which was chromatographed using activated magnesium silicate and graded methanol/chloroform solvent mixtures. The fractions were monitored by thin layer chromatography and the desired material was obtained from the 2% methanol/chloroform fractions. The appropriate fractions were combined and evaporated to give 1.2 g. (51%) of golden gum. The material was pure by thin layer chromatography (10% MeOH/CHCl₃), and the infrared and nuclear magnetic resonance spectra were in agreement with the proposed structure.

Analysis Calcd. for $C_{33}H_{51}NO_4$ (MW = 525.73): C, 75.39; H, 9.78; N, 2.66. Found: C, 75.44; H, 9.81; N, 2.65.

EXAMPLE 37

1-[2-Methyl-4-(morpholino)butyryloxy]-3-(3-methyl-2-octyl)-7,8,9,10-tetrahydro-6,6,10-trimethyl-6H-dibenzo[b,d]pyran A. Ethyl 2-methyl-4-morpholinobutyrate A mixture of 40.0 g. (0.19 mole) of ethyl 4-bromo-2-methylbutyrate (Tetrahedron 21, 2966 (1965)), 66.0 g. (0.76 mole) of morpholine and 750 ml. of benzene was heated at 60°C. for 5 hours and stirred at room temperature for a total of 40 hours. A colorless solid was removed by filtration, and the mother liquor was evaporated to give a colorless, mobile residue. This material was combined with 250 ml. of ether and filtered to remove a small amount of additional solid. The solution was concentrated and the residue distilled to give the desired material as 38.0 g. (93%) of colorless liquid (b.p. 71°–73°C. at 0.10 mm).

B. 2-Methyl-4-morpholinobutyric acid hydrochloride 32.0 g. (0.15 mole) of ethyl 2-methyl-4-morpholinobutyrate was combined with 200 ml. of concentrated hydrochloric acid and 200 ml. of water and refluxed with stirring for 20 hours. The solution was concentrated on a rotary evaporator to give a viscous, colorless residue. This material was triturated with acetone, filtered and dried to give 30.6 g. (92%) of colorless crystals, m.p. 155°–157°C.

C. 1-[2-Methyl-4-(morpholino)butyryloxy]-3-(3-methyl-2-octyl)-7,8,9,10-tetrahydro-6,6,10-trimethyl-6H-dibenzo[b,d]pyran A mixture of 1.2 g. (3.24 mmole) of 1-hydroxy-3-(3-methyl-2-octyl)-7,8,9,10-tetrahydro-6,6,10-trimethyl-6H-dibenzo[b,d]pyran, 0.73 g. (3.24 mmole) of 2-methyl-4-morpholinobutyric acid hydrochloride, 0.71 g. (3.46 mmole) of dicyclohexylcarbodiimide and 50 ml. of methylene chloride was stirred at room temperature for 16 hrs. The reaction mixture was cooled and the byproduct of dicyclohexylurea was removed by filtration. The solvent was evaporated to give a foamy residue which was chromatographed using activated magnesium silicate and methanol/chloroform solvent mixtures. The fractions were monitored by thin layer chromatography and the desired material was obtained from the 2% methanol/chloroform fractions. The appropriate fractions were collected and evaporated to give 0.9 g. (51%) of light purple gum.

Analysis Calcd. for $C_{34}H_{53}NO_4$ (MW = 539.76): C, 75.65; H, 9.89; N, 2.59. Found: C, 75.76; H, 9.88; N, 2.49.

The foregoing detailed description has been given for clearness of understanding only, and no unnecessary limitations should be understood therefrom, as modifications will be obvious to those skilled in the art.

We claim:

1. A compound represented by the formulae:

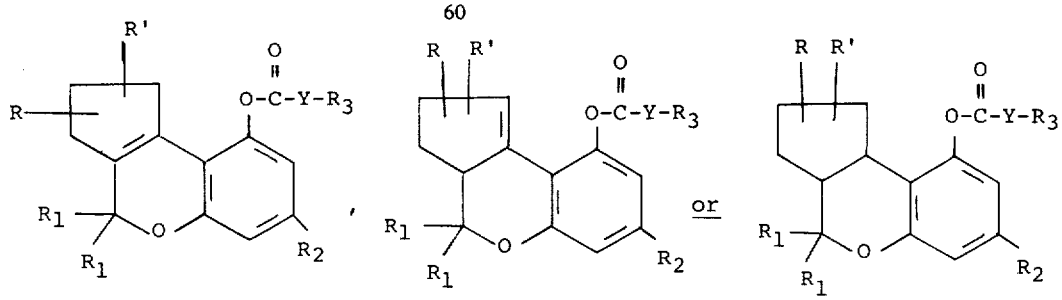

wherein R and R' are hydrogen or $C_1$–$C_6$ alkyl; $R_1$ is $C_1$–$C_6$ alkyl; $R_2$ is $C_1$–$C_{20}$ alkyl; Y is a straight or branched chain $C_1$–$C_8$ alkylene; and $R_3$ is

 , and

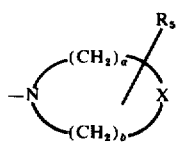

wherein $a$ is 2, $b$ is 2, X is O, S or $NR_4$ wherein $R_4$ is hydrogen or a $C_1$–$C_6$ alkyl and $R_5$ is hydrogen or a $C_1$–$C_6$ alkyl, or a pharmaceutically acceptable acid addition salt thereof.

2. A compound in accordance with claim 1: 4,4-dimethyl-7-(3-methyl-2-octyl)-9-[4-(piperidino)-butyryloxy]-1,2,3,4-tetrahydrocyclopenta[c][1]benzopyran or a pharmaceutically acceptable acid addition salt thereof.

3. A compound in accordance with claim 1: 4,4-dimethyl-7-(3-methyl-2-octyl)-9-[3-(piperidino)propionyloxy]-1,2,3,4-tetrahydrocyclopenta[c][1]benzopyran or a pharmaceutically acceptable acid addition salt thereof.

4. A compound in accordance with claim 1: 4,4-dimethyl-7-(3-methyl-2-octyl)-9-[4-(morpholino)-butyryloxy]-1,2,3,4-tetrahydrocyclopenta[c][1]benzopyran or a pharmaceutically acceptable acid addition salt thereof.

5. A compound in accordance with claim 1: 4,4-dimethyl-9-[4-(morpholino)butyryloxy]-7-pentyl-1,2,3,4-tetrahydrocyclopenta[c][1]benzopyran or a pharmaceutically acceptable acid addition salt thereof.

6. A compound in accordance with claim 1: 4,4-dimethyl-7-(3-methyl-2-octyl)-9-[4-(pyrrolidino)-butyryloxy]-1,2,3,4-tetrahydrocyclopenta[c][1]benzopyran or a pharmaceutically acceptable acid addition salt thereof.

7. A compound in accordance with claim 1: 4,4-dimethyl-9-[4-(homopiperidino)butyryloxy]-7-(3-methyl-2-octyl)-1,2,3,4-tetrahydrocyclopenta[c][1]benzopyran or a pharmaceutically acceptable acid addition salt thereof.

8. A compound in accordance with claim 1: 4,4-dimethyl-9-[4-(homopiperidino)butyryloxy]-7-pentyl-1,2,3,4-tetrahydrocyclopenta[c][1]benzopyran.

9. A compound in accordance with claim 1: 4,4-dimethyl-9-[pyrrolidino)butyryloxy]-7-pentyl-1,2,3,4-tetrahydrocyclopenta[c][1]benzopyran.

10. A compound in accordance with claim 1: 4,4-dimethyl-9-[4-(thiomorpholino)butyryloxy]-7-(3-methyl-2-octyl)-1,2,3,4-tetrahydrocyclopenta[c][1]benzopyran or a pharmaceutically acceptable acid addition salt thereof.

11. A compound represented by the formulae:

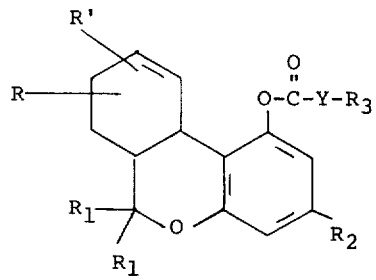

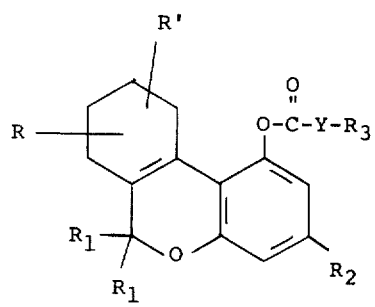

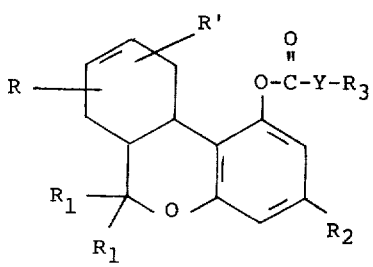 or

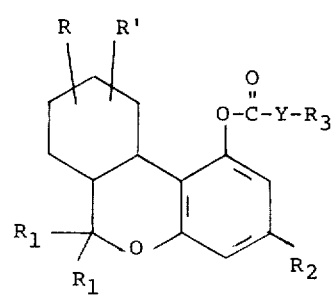

wherein R and R' are hydrogen or $C_1$–$C_6$ alkyl; $R_1$ is $C_1$–$C_6$ alkyl; $R_2$ is $C_1$–$C_{20}$ alkyl, Y is a straight or branched chain $C_1$–$C_8$ alkylene; and $R_3$ is

and

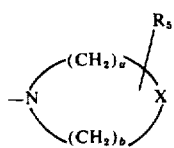

wherein $a$ is 2, $b$ is 2, X is O, S or $NR_4$ wherein $R_4$ is hydrogen or a $C_1$–$C_6$ alkyl and $R_5$ is hydrogen or a $C_1$–$C_6$ alkyl, or a pharmaceutically acceptable acid addition salt thereof.

12. A compound in accordance with claim 11: 1-[4-(morpholino)butyryloxy]-3-n-pentyl-6,6,9-trimethyl-6a,7,8,10a-tetrahydrodibenzo[b,d]pyran, or a pharmaceutically acceptable acid addition salt thereof.

13. A compound in accordance with claim 11: 3-n-pentyl-1-[4-(piperidino)butyryloxy]6,6,9-trimethyl-6a,7,8,10,a-tetrahydrodibenzo[b,d]pyran, or a pharmaceutically acceptable acid addition salt thereof.

14. A compound in accordance with claim 11: 3-(3-methyl-2-octyl)-1-[4-(morpholino)butyryloxy]-6,6,9-trimethyl-7,8,9,10-tetrahydro-6H-dibenzo[b,d]pyran, or a pharmaceutically acceptable acid addition salt thereof.

15. A compound in accordance with claim 11: 3-(3-methyl-2-octyl)-1-[4-(piperidino)butyryloxy]-6,6,9-trimethyl-7,8,9,10-tetrahydro-6H-dibenzo[b,d]pyran or a pharmaceutically acceptable acid addition salt thereof.

16. A compound in accordance with claim 11: 1-[4-homopiperidino)butyryloxy]-3-(3-methyl-2-octyl)-6,6,9-trimethyl-7,8,9,10-tetrahydro-6H-dibenzo[b,d]-pyran or a pharmaceutically acceptable acid addition salt thereof.

17. A compound in accordance with claim 11: 3-(3-methyl-2-octyl)-1-[4-(morpholino)butyryloxy]-6,6,9-trimethyl-6a,7,10,10a-tetrahydrodibenzo[b,d]pyran or a pharmaceutically acceptable acid addition salt thereof.

18. A compound in accordance with claim 11: 1-[4-thiomorpholino)butyryloxy]-3-(3-methyl-2-octyl)-6,6,9-trimethyl-7,8,9,10-tetrahydro-6H-dibenzo[b,d]-pyran or a pharmaceutically acceptable acid addition salt thereof.

19. A compound in accordance with claim 11: 3-(3-methyl-2-octyl)-1-[4-(morpholino)butyryloxy]-7,8,9,10-tetrahydro-6,6,10-trimethyl-6H-dibenzo[b,d]pyran or a pharmaceutically acceptable acid addition salt thereof.

20. A compound in accordance with claim 11: 1-[2-methyl-4-(morpholino)-butyryloxy]-3-(3-methyl-2-octyl)-7,8,9,10-tetrahydro-6,6,10-trimethyl-6H-dibenzo[b,d]pyran or a pharmaceutically acceptable acid addition salt thereof.

* * * * *

UNITED STATES PATENT AND TRADEMARK OFFICE
CERTIFICATE OF CORRECTION

PATENT NO. : 3,941,782
DATED : March 2, 1976
INVENTOR(S) : Louis Selig Harris et al.

It is certified that error appears in the above–identified patent and that said Letters Patent are hereby corrected as shown below:

Column 2, line 24, "meleate" should be --maleate--; column 4, line 54, "J. chem." should be --J. Chem.--; column 5, line 14, "]1]" should be --[1]--; line 27, "pentyl 6a" should be --pentyl-6a--; line 28, "-methyl-" should be deleted from "-methyl-9-hydroxy-"; line 46, "[3-pyrrolidino)-" should be -- [3-(pyrrolidino)- --; line 55, "10a hexahydro" should be -- 10a-hexahydro- --; line 59, "pharmaceuticlly" should be --pharmaceutically--; line 62, insert --forms-- after "dosage"; column 6, line 7, "accpetable" should be --acceptable--; column 7, line 12, "cooked" should be --cooled--; column 8, line 46, change "3n" to --3-n--; column 9, line 35, "-7n" should be -- -7-n --; line 36, "tetrahydroxycyclopenta[[c]" should be --tetrahydrocyclopenta[c]--; line 60, "3n" should be -- 3-n --; column 10, line 34, "49.601" should be --49.60;--; column 12, line 8, "evaporation" should be --evaporator--; line 25, delete the first bracket in "dibenzo[[b,d]"; column 14, line 20, "1-[4-Homopiperidino)" should be -- 1-[4-(Homopiperidino) --; column 15, line 45, "given" should be --giving--; line 57, change "9[4" to -- 9-[4 --; line 67, "to" should be --To--; column 26, line 5, "10,a" should be --10a--; line 28, change "thiomorpholino)" to --(thiomorpholino)--.

Signed and Sealed this twenty-second Day of June 1976

[SEAL]

Attest:

RUTH C. MASON
Attesting Officer

C. MARSHALL DANN
Commissioner of Patents and Trademarks